United States Patent [19]

Kendall-Tobias

[11] Patent Number: 4,617,953
[45] Date of Patent: Oct. 21, 1986

[54] FLUID FLOW CONTROL SYSTEM

[76] Inventor: Michael W. Kendall-Tobias, 3 Greenfield Ave., Danbury, Conn. 06810

[21] Appl. No.: 670,714

[22] Filed: Nov. 13, 1984

[51] Int. Cl.$^4$ .............................................. F16K 7/12
[52] U.S. Cl. .................................... 137/110; 137/114
[58] Field of Search ................. 137/110; 251/45, 61.1; 137/114

[56] References Cited

U.S. PATENT DOCUMENTS 3,447,775  6/1969  Katchka ................................ 251/45
3,470,896  10/1969  Werter ................................. 137/110

Primary Examiner—Alan Cohan

[57] ABSTRACT

A system which is especially useful in controlling fuel gas flow in a flame atomic absorption spectrophotometer includes a master fluid flow path and a slave fluid flow path connected to receive fluid from a common source connection. A first valve is connected in the master path for controlling the rate of fluid flow therein. A first orifice device is connected in the master path between the common source connection and the first valve. The slave path includes a pressure responsive fluid flow modulating valve having a control connection to the master path between the first orifice device and the first valve. A second orifice device is connected in the slave path between the common source connection and the flow modulating valve. The flow modulating valve is operable in response to the fluid pressure in the master path as reduced by the first orifice device and in response to the fluid pressure in the slave path as reduced by the second orifice device to control the fluid flow through the slave path.

11 Claims, 1 Drawing Figure

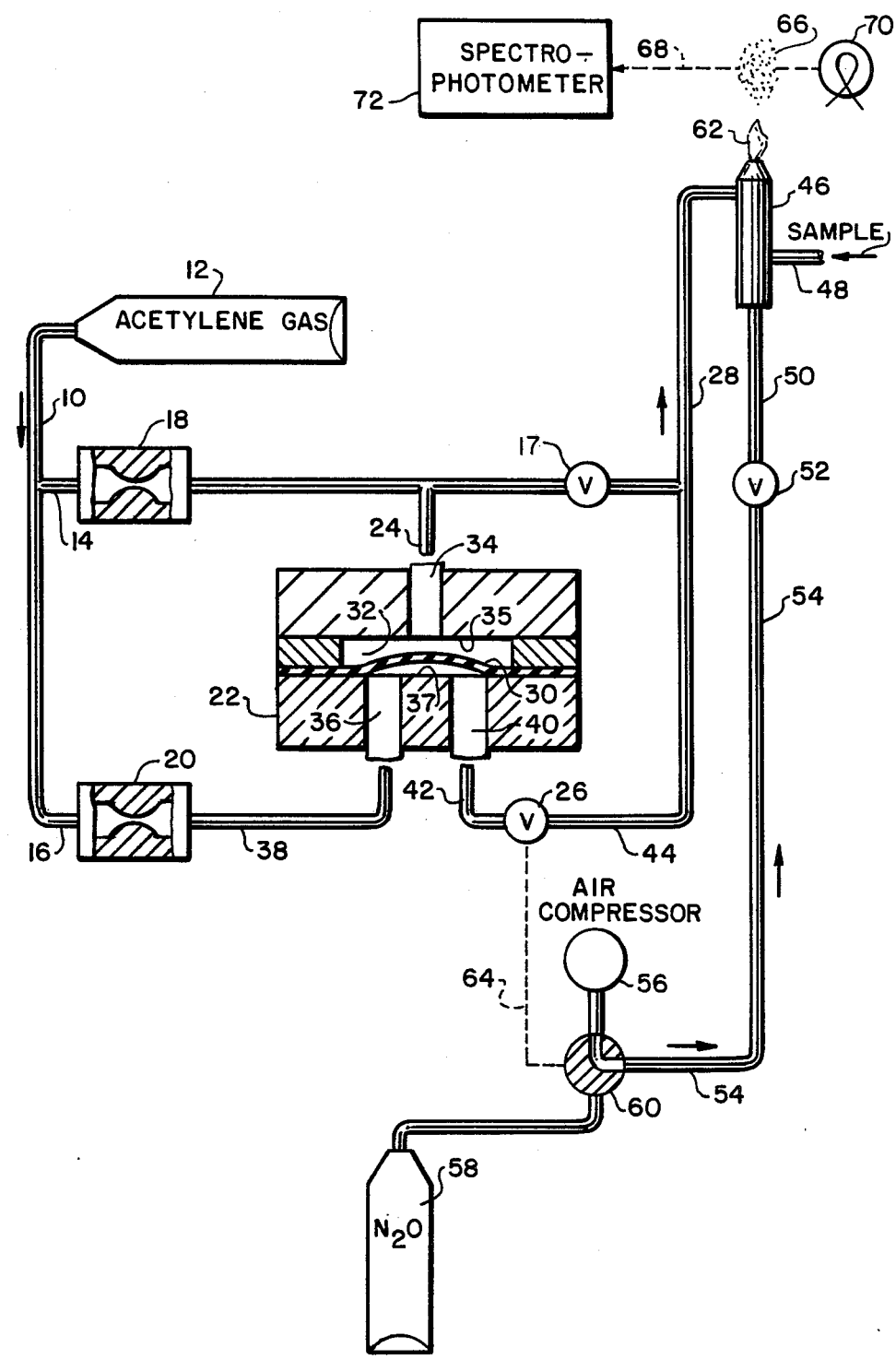

FLUID FLOW CONTROL SYSTEM

BACKGROUND OF THE INVENTION

The present invention relates to a fluid flow control system which is especially useful in providing a rate of fluid flow in a slave path which is directly related to the rate of fluid flow in a master path, and which is particularly useful in the control of fuel gas in a flame atomic absorption spectrophotometer.

In atomic absorption spectroscopy, the measurement of the absorption of a radiation beam at a characteristic resonant spectral line for a particular element yields a measure of the concentration of that element in an original sample solution. Presently, one of the most common techniques for atomizing an element for purposes of the absorption measurement is by introducing a liquid sample solution of the element of interest into a gas burner wherein droplets of the solution are vaporized and the elements ultimately atomized, so as to form in the path of the apparatus radiation beam, a substantial quantity of the element of interest in its atomic state. A sample light beam, which originates from a line-emitting light source, such as a hollow-cathode lamp and which includes a resonance line of the element to be measured, is directed through the flame. The desired element in the sample absorbs the resonance lines characteristic of the element and the emerging light beam is directed to a monochromator and thence to a detector which measures the degree to which the desired element absorbs the resonance lines of the sample beam. This absorption degree represents the amount of desired element in the sample substance.

In such spectrophotometers, in order to produce a flame which has a high enough temperature for the best measurement results, for certain elements it is preferred to use acetylene gas as a fuel and to use nitrous oxide ($N_2O$) as the source of oxygen for the combustion of the acetylene gas. In order to initiate combustion in a safe manner, it is necessary to begin combustion of the acetylene gas using air as the oxygen source, and to then switch over to the nitrous oxide after the acetylene gas flame is ignited and stable.

However, upon switching over from air to nitrous oxide, it is necessary to essentially double the flow of acetylene gas to the flame in order to maintain the proper ratio of fuel to oxidant. It is also desirable to carefully regulate the ratio of fuel to oxidant by means of valves in the respective fuel and oxidant lines, and to avoid having that mixture adjustment altered detrimentally by the changeover from air to nitrous oxide and the doubling of the acetylene gas flow. Heretofore, this maintenance of fuel oxidant mixture during changeover from air to nitrous oxide has been a difficult problem.

Accordingly, it is one important object of the present invention to provide a fuel flow control system which is operable to provide controlled fuel flow rates at two different levels depending on whether the oxygen source is air or nitrous oxide.

Another object of the invention is to provide a fluid flow system in which the flow in a slave path is made to follow the rate of flow in a master path.

Other objects and advantages of the invention will be apparent from the following description and the accompanying drawings.

SUMMARY OF THE INVENTION

In carrying out the invention there is provided a fluid flow control system comprising a common source connection for a fluid under pressure, a master fluid flow path and a slave fluid flow path connected to receive fluid from said common source connection, a first valve means connected in said master path for controlling the rate of fluid flow therein, a first orifice device connected in said master path between said common source connection and said first valve means, said slave path including a pressure responsive fluid flow modulating means connected in series therein and having a control connection to said master path between said first orifice device and said first valve means, a second orifice device connected in said slave path between said common source connection and said flow modulating means, said first and second orifice devices each being operable to provide pressure drops in response to fluid flow as measures of fluid flow through said master and slave paths respectively, said flow modulating means being operable in response to the fluid pressure in said master path as reduced by said first orifice device and in response to the fluid pressure in said slave path as reduced by said second orifice device to control the fluid flow through said slave path and the resultant pressure drop through said second orifice device to maintain a predetermined relationship to the fluid flow through said master path.

BRIEF DESCRIPTION OF THE DRAWING

The drawing is a schematic representation of a system in accordance with the present invention for supplying combustion gas and an oxygen source gas to an atomic absorption spectrophotometer.

DETAILED DESCRIPTION

Referring particularly to the drawing, there is illustrated a fluid flow control system including a common source connection 10 for fluid under pressure, such as acetylene from an acetylene gas container 12. A master fluid flow path 14 and a slave fluid flow path 16 are connected to receive fluid from the common source connection 10. The master path 14 includes a first valve 17 for controlling the rate of fluid flow therethrough. The master path also includes a first orifice device 18 connected in the master path between the common source 10 and the first valve 16.

The slave path 16 includes a second orifice device 20 and a flow modulating valve 22 connected in series. The flow modulating valve 22 includes a control connection 24 to the master path 14 between the first orifice device 18 and the first valve 16. The slave path also preferably includes a shut-off valve 26, which is shown positioned on the downstream side of the flow modulating valve 22, but which may be positioned anywhere in the slave path. The downstream ends of the master and slave paths may preferably connect to a common delivery connection 28.

Assuming the shut-off valve 26 is open, the orifice devices 18 and 20, and the fluid flow modulating valve 22 operate to maintain the rate of flow in the slave path 16 at a predetermined relationship to the rate of flow in the master path 14. In a preferred embodiment, the flow rate in the slave path is maintained at a rate substantially equal to the flow rate through the master path 14. To accomplish this result, the orifice devices 18 and 20 are substantially identical, providing substantially equal restrictions to flow, and thus causing equal pressure drops in response to flow. The flow modulating valve 22 responds to the pressures on the downstream sides of the orifices 18 and 20 (the supply pressure as reduced by those respective orifices) to control the flow in the slave path 16 to maintain that flow substantially equal to the flow through the master path 14.

For accomplishing this purpose, the flow modulating valve 22 includes an interior diaphragm 30 which is composed of rubber, or a rubber-like material (which are collectively referred to below as "rubber-like"). The diaphragm is mounted within a chamber 32 which is in communication, through a port 34, with the connection 24 from the master path 14. The port 34 extends through an inner wall 35. The underside of the diaphragm is in communication with the slave path through a port 36 at a connection 38 from the downstream side of the orifice device 20. Port 36 extends through a wall 37. The diaphragm 30 is mounted essentially against wall 37. If the pressure in the master path 14 at connection 24 exceeds the pressure in the slave path 16 at connection 38, the resultant pressure in chamber 32 forces the diaphragm 30 into a flattened state in which it covers the port 36 and prevents flow in the slave path 16. However, if the pressures in the master and slave paths at 24 and 38 are not substantially equal, and if the pressure in the slave path exceeds the pressure in the master path, then the diaphragm 30 is forced upwardly from the port 36, as indicated in the drawing, opening that port, and permitting flow of fluid through the adjacent and associated port 40, which also extends through wall 37, and thus through the portion of the slave path indicated by connection 42, the valve 26, and connection 44.

In operation, the flow modulating valve 22 operates to maintain the flows at equal rates through the two paths. If the flow rate through the slave path 16 is less than the flow rate through the master path 14, then the pressure drop through the orifice device 20 will be less than the pressure drop through the orifice device 18. The result will be that the pressure in the slave path 16 at connection 38 will exceed the pressure in the master path 14 at 24. This will cause the diaphragm 30 to open more completely, providing for an increased flow through the slave path until the pressure drop through the orifice device 20 increases to be about the same as the pressure drop through orifice device 18. On the other hand, if the flow through the slave path should somehow increase beyond that of the flow in the master path 14, then the pressure drop in the orifice device 20 will increase beyond that of the pressure drop in orifice device 18. The result is that the pressure in slave path connection 38 will be less than the pressure in master path connection 24. This will tend to close down the diaphragm 30 of the modulating valve 22 to correspondingly reduce the flow in the slave path 16. Thus, the balance of pressures on the modulating valve 22 serves to modulate the flow of fluid through the slave path to maintain that flow substantially equal to the flow through the master path.

These principles of operation apply even though the rate of flow through the master path is controlled by the valve 16. Thus, if the valve 16 is partly closed down, reducing the flow in the master path, the increase in pressure in the master path at connection 24 resulting from the reduced pressure drop through the orifice device 18 causes the modulating valve 22 to partially close, restricting the flow in the slave path through valve 22 until it substantially corresponds to the rate of flow through the master path.

It will be understood, of course, that because of the slight spring force introduced by the elasticity of the diaphragm 30, the regulation of pressures in the master path and the slave path may not be exactly equal. However, for practical purposes, the regulation is very close to being equal.

In a preferred embodiment of the invention, it is combined in a fuel supply system for a flame atomic absorption spectrophotometer. In such a combination, as illustrated in the drawing, the fluid supplied to the common input connection 10 is acetylene gas from the container 12, and the acetylene gas supplied through the common output connection 28 is connected to provide fuel to a burner chamber 46. A liquid sample of the material to be analyzed is supplied at connection 48 to a nebulizer within the burner chamber, and a source of oxygen for combustion is supplied under pressure through connection 50 and the valve 52. The valve 52 is provided for controlling the rate of oxygen-bearing gas supplied from a connection 54. The source of oxygen-bearing gas is preferably either an air compressor 56, or a container 58 of nitrous oxide. A selector valve 60 is provided to select either air from the compressor 56 or nitrous oxide from the container 58. The valve 60 is illustrated in the position selecting air, which is the typical starting position for the valve 60. When nitrous oxide is to be selected, the valve 60 is rotated 90 degrees clockwise, so that the internal passage connects the nitrous oxide to the connection 54.

In the typical mode of operation, the burner, which is at the top of the nebulizer 46, is started with the combination of air from the compressor 56, and the acetylene gas, to form the flame as indicated at 62. However, after combustion begins, and is stable, the system is shifted to use nitrous oxide, by rotation of the selector valve 60. At that time, the flow of acetylene gas must be substantially doubled. In order to accomplish this, simultaneously with the selection of nitrous oxide by rotation of valve 60, the slave path 16 is opened up by opening the valve 26. This may be accomplished by a coupling, either mechanical or electrical, indicated in the drawing schematically by means of the dotted connection 64 between the valve 60 and the valve 26.

As long as shut-off valve 26 is closed, there can be no flow through the slave path 16, and the automatic flow control provided by the orifice devices 18 and 20 and the flow modulating valve 22 is not effective to maintain flow through the slave path 16. However, as soon as valve 26 is opened, that system is effective. After the system is operating on nitrous oxide, with the doubled flow rate of acetylene gas, the sample to be tested is introduced 25 through connection 48 into the nebulizer 46, the sample is vaporized, as indicated at 66 above the flame 62, and the beam of light 68 from the light source 70 is partially absorbed by that vapor 66 before it is received at the spectrophotometer schematically indicated at 72. It will be understood that the light source 70 and the spectrophotometer 72 are only schematically shown, and suitable lenses and reflectors, and other optical elements, will be employed in connection with these devices.

The selector valve 60 and the shut-off valve 26 are schematically shown. A more detailed disclosure of a preferred arrangement of these valves is to be formed in a co-pending U.S. patent application Ser. No. (670,713) filed concurrently with the present application by the present inventor for IMPROVED SYSTEM FOR CHANGING OXIDANTS IN A FLAME ATOMIC ABSORPTION SPECTROPHOMETER and assigned to the same assignee as the present invention now U.S. Pat. No. 4,571,172.

While one preferred embodiment and example of the flow control portion of the system has been illustrated and described in conjunction with the drawing, it will be apparent that other embodiments may be made which provide flows in the slave path which are different functions of the flow in the master path. For instance, the orifice devices 18 and 20 may be unequal, with the result that the flow in the slave path will be a function of the flow in the master path, but not equal. Furthermore, the flow modulating valve 22 may be embodied in other ways, such as by means of a compound piston, having piston lands and cylinders of different sizes for the master path and slave path, so as to provide a ratio of pressures rather than equal pressures in the two paths. Furthermore, such a piston may be spring biased in one direction, to provide a pressure offset in the pressure of one path in relation to the pressure in the other.

In still other variations, more than one slave path may be provided and coupled to the master path 14. In still another variation, a second slave path (not shown) may be controlled by the slave path 16, slave path 16 operating as a master path with respect to that new slave path.

While this invention has been shown and described in connection with particular preferred embodiments, various alterations and modifications will occur to those skilled in the art. Accordingly, the following claims are intended to define the valid scope of this invention over the prior art, and to cover all changes and modifications falling within the true spirit and valid scope of this invention.

What is claimed is:

1. A fluid flow control system comprising a common source connection for a fluid under pressure, a master fluid flow path connected to receive fluid from said common source connection, at least one slave fluid flow path connected to receive fluid from said common source connection, a first valve means connected in said master path for controlling the rate of fluid flow therein, means operable to maintain the rate of fluid flow in said slave path at a predetermined relationship to the rate of flow in said master path comprising a first orifice device connected in said master path between said common source connection and said first valve means, said slave path including a pressure responsive fluid flow modulating means connected in series therein and having a control connection to said master path between said first orifice device and said first valve means, a second orifice device connected in said slave path between said common source connection and said flow modulating means, said first and second orifice devices each being operable to provide pressure drops in response to fluid flow as measures of fluid flow through said master and slave paths respectively, said flow modulating means being operable in response to the fluid pressure in said master path as reduced by said first orifice device as detected through said control connection and operable in response to the fluid pressure in said slave path as reduced by said second orifice device to control the fluid flow through said slave path and the resultant pressure drop through said second orifice device to maintain a predetermined relationship of the fluid flow through said slave path to the fluid flow through said master path by maintenance of a predetermined relationship between the fluid pressures in said master and slave paths as detected at said modulating valve;

said flow modulating means being operable to maintain a predetermined relationship between said master and slave path fluid pressures which consists of a substantially constant ratio between said pressures, the constant ratio being one to one;

said first and second orifice devices having substantially equal sized orifices to provide for substantially equal pressure drops in response to equal fluid flows;

the downstream end of said master path beyond said first valve means being connected in common to the downstream end of said slave path beyond said flow modulating means to a common delivery connection, and a second valve means connected in said slave path which is operable to shut off all flow from said slave path when slave path flow is not required.

2. A system as claimed in claim 1 which is particularly adapted to deliver acetylene gas as a fuel for a flame spectrophotometer apparatus wherein a source of acetylene gas is connected to said common source connection for delivering acetylene gas as the fluid under pressure, and wherein there is provided a means connected to said common delivery connection for mixing said acetylene gas with an oxygen bearing gas to provide a combustible mixture for the flame of the spectrophotometer, a delivery line for oxygen bearing gas connected to said mixing means for delivery of oxygen bearing gas thereto, a selectively operable valve means connected to said oxygen bearing gas delivery line for selectively delivering pressurized air or nitrous oxide as the oxygen bearing gas, said selectively operable valve means being operable in conjunction with the operation of said second valve means to open said second valve means when said selectively operable valve means is operated to deliver nitrous oxide to thereby increase the delivery of acetylene gas by opening said slave path whenever nitrous oxide is supplied as the oxygen bearing gas.

3. A system as claimed in claim 2 wherein said fluid flow modulating means comprises a fluid flow modulating valve including a pressure chamber and three ports into said chamber, two of said ports entering said chamber through a first wall of said chamber and being connected in series in said slave path, a diaphragm of a rubber-like material arranged against said first wall of said chamber, a third one of said ports of said valve communicating with said chamber through a second wall of said chamber and being connected to said control connection to said master path, said diaphragm being operable to be distended in response to the balance of pressures as conveyed through said ports from said master path and said slave path to open and close the connection between said first and second ports in said common wall and to vary the opening of said connection in response to said balance of pressures to thereby modulate the fluid flow in said slave path.

4. A fluid flow control system comprising a common source connection for a fluid under pressure, a master fluid flow path connected to receive fluid from said common source connection, at least one slave fluid flow path connected to receive fluid from said common source connection, a first valve means connected in said master path for controlling the rate of fluid flow therein, means operable to maintain the rate of fluid flow in said slave path at a predetermined relationship to the rate of flow in said master path comprising a first orifice device connected in said master path between said common source connection and said first valve means, said slave path including a pressure responsive fluid flow modulating means connected in series therein and having a control connection to said master path between said first orifice device and said first valve means, a second orifice device connected in said slave path between said common source connection and said flow modulating means, said first and second orifice devices each being operable to provide pressure drops in response to fluid flow as measures of fluid flow through said master and slave paths respectively, said flow modulating means being operable in response to the fluid pressure in said master path as reduced by said first orifice device as detected through said control connection and operable in response to the fluid pressure in said slave path as reduced by said second orifice device to control the fluid flow through said slave path and the resultant pressure drop through said second orifice device to maintain a predetermined relationship of the fluid flow through said slave path to the fluid flow through said master path by maintenance of a predetermined relationship between the fluid pressures in said master and slave paths as detected at said modulating valve;

the downstream end of said master path beyond said first valve means being connected in common to the downstream end of said slave path beyond said flow modulating means to a common delivery connection, and a second valve means connected in said slave path which is operable to shut off all flow from said slave path when slave path flow is not required.

5. A system as claimed in claim 4 wherein said flow modulating means is operable to maintain a predetermined relationship between said master and slave path fluid pressures which consists of a substantially constant ratio between said pressures.

6. A system as claimed in claim 5 wherein the constant ratio is one to one.

7. A system as claimed in claim 6 wherein said fluid flow modulating means comprises a fluid flow modulating valve including a pressure chamber and three ports into said chamber, two of said ports entering said chamber through a first wall of said chamber and being connected in series in said slave path, a diaphragm of a rubber-like material arranged against said first wall of said chamber, a third one of said ports of said valve communicating with said chamber through a second wall of said chamber and being connected to said control connection to said master path, said diaphragm being operable to be distended in response to the balance of pressures as conveyed through said ports from said master path and said slave path to open and close the connection between said first and second ports in said common wall and to vary the opening of said connection in response to said balance of pressures to thereby modulate the fluid flow in said slave path.

8. A system as claimed in claim 4 wherein said first and second orifice devices have substantially equal sized orifices to provide for substantially equal pressure drops in response to equal fluid flows.

9. A system as claimed in claim 4 wherein said first and second orifice devices have orifices which are different in size so as to provide for different pressure drops as functions of fluid flow volume.

10. A system as claimed in claim 4 wherein the downstream end of said master path beyond said first valve means is connected in common to the downstream end of said slave path beyond said flow modulating means to a common delivery connection, and wherein there is provided a second valve means connected in said slave path which is operable to shut off all flow from said slave path when slave path flow is not required.

11. A system as claimed in claim 6 wherein said first and second orifice devices have substantially equal sized orifices to provide for substantially equal pressure drops in response to equal fluid flows.

* * * * *